(12) United States Patent
Neuman et al.

(10) Patent No.: US 11,260,359 B2
(45) Date of Patent: Mar. 1, 2022

(54) INCORPORATION OF CHITOSAN IN MICROCAPSULE WALL

(71) Applicant: Encapsys, LLC, Appleton, WI (US)

(72) Inventors: Presley Genevie Neuman, Appleton, WI (US); Linsheng Feng, Menasha, WI (US)

(*) Notice: Subject to any disclaimer, the term of this patent is extended or adjusted under 35 U.S.C. 154(b) by 162 days.

(21) Appl. No.: 16/739,195

(22) Filed: Jan. 10, 2020

(65) Prior Publication Data

US 2020/0222873 A1 Jul. 16, 2020

Related U.S. Application Data

(60) Provisional application No. 62/791,148, filed on Jan. 11, 2019.

(51) Int. Cl.
*B01J 13/14* (2006.01)
*C11B 9/00* (2006.01)

(52) U.S. Cl.
CPC ............... *B01J 13/14* (2013.01); *C11B 9/00* (2013.01)

(58) Field of Classification Search
CPC ......... B01J 13/14; B01J 13/10; B01J 13/206; B01J 13/185; C11B 9/00; A61K 9/5036; A01N 25/28; A23P 10/30
See application file for complete search history.

(56) References Cited

U.S. PATENT DOCUMENTS

| | | | |
|---|---|---|---|
| 5,562,924 A * | 10/1996 | Perrier | A61K 9/1652 424/499 |
| 5,691,060 A | 11/1997 | Levy | |
| 5,705,270 A | 1/1998 | Soon-Shiong et al. | |
| 5,753,264 A * | 5/1998 | Magdassi | A01N 25/04 424/451 |
| 6,242,099 B1 * | 6/2001 | Grandmontagne | A61K 8/11 428/402.2 |
| 8,404,345 B2 | 3/2013 | Naylor Rocha Gomes et al. | |
| 8,765,659 B2 | 7/2014 | Gizaw et al. | |
| 9,242,028 B2 | 1/2016 | Saunders et al. | |
| 2002/0022038 A1 | 2/2002 | Biatry et al. | |
| 2011/0027376 A1 | 2/2011 | Boey et al. | |
| 2011/0171349 A1 | 7/2011 | Poortinga et al. | |
| 2013/0330292 A1 | 12/2013 | Lei et al. | |
| 2014/0186630 A1 * | 7/2014 | Schwantes | A01N 25/28 428/402.24 |
| 2016/0106636 A1 | 4/2016 | Speaker et al. | |
| 2016/0166480 A1 | 6/2016 | Lei et al. | |
| 2018/0042825 A1 | 2/2018 | Lei et al. | |
| 2018/0265818 A1 | 9/2018 | Smets et al. | |

FOREIGN PATENT DOCUMENTS

| | | | | |
|---|---|---|---|---|
| CN | 101879427 | * | 11/2010 | |
| EP | 1101527 A1 | * | 5/2001 | ............. B01J 13/04 |
| EP | 1243320 | | 2/2005 | |
| EP | 1243318 | | 3/2005 | |
| WO | 2003086104 | | 10/2003 | |
| WO | 2005014698 | | 2/2005 | |
| WO | 2005105291 | | 11/2005 | |
| WO | 2006117702 | | 10/2007 | |
| WO | 2009037482 | | 3/2010 | |
| WO | 2015031418 | | 3/2015 | |
| WO | 2016014734 | | 1/2016 | |
| WO | 2018053356 | | 3/2018 | |
| WO | 2019063515 | | 4/2019 | |

OTHER PUBLICATIONS

Younes I, Rinaudo M., "Chitin and chitosan preparation from marine sources. Structure, properties and applications." Mar Drugs. 2015;13(3):1133-1174. Published Mar. 2, 2015. doi: 10.3390/md13031133.

Mohammed Reza Kasaai, Joseph Arul, Gerard Charlet, "Fragmentation of Chitosan by Acids", The Scientific World Journal, vol. 2013, Article ID 508540, 11 pages, 2013. https://doi.org/10.1155/2013/508540.

* cited by examiner

*Primary Examiner* — Irina S Zemel
(74) *Attorney, Agent, or Firm* — Benjamin Mieliulis

(57) ABSTRACT

The microcapsules and process of making describe a novel core shell microcapsule. The microcapsule incorporates a polysaccharide such as chitosan into the microcapsule wall forming the shell. The microcapsule shell is formed by dissolving chitosan into a material of structure

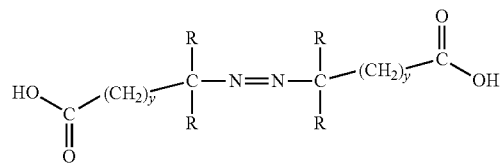

wherein each R is independently selected from hydrogen, $C_1$ to $C_8$ alkyl, or a cyano group; and each y is independently an integer from 1 to 8, and reacting with a multifunctional (meth)acrylate.

21 Claims, No Drawings

INCORPORATION OF CHITOSAN IN MICROCAPSULE WALL

FIELD OF THE INVENTION

This invention relates to capsule manufacturing processes and microcapsules produced by such processes.

DESCRIPTION OF THE RELATED ART

Various processes for microencapsulation, and exemplary methods and materials are set forth in Schwantes (U.S. Pat. No. 6,592,990), Nagai et al. (U.S. Pat. No. 4,708,924), Baker et al. (U.S. Pat. No. 4,166,152), Wojciak (U.S. Pat. No. 4,093,556), Matsukawa et al. (U.S. Pat. No. 3,965,033), Matsukawa (U.S. Pat. No. 3,660,304), Ozono (U.S. Pat. No. 4,588,639), Irgarashi et al. (U.S. Pat. No. 4,610,927), Brown et al. (U.S. Pat. No. 4,552,811), Scher (U.S. Pat. No. 4,285,720), Shioi et al. (U.S. Pat. No. 4,601,863), Kiritani et al. (U.S. Pat. No. 3,886,085), Jahns et al. (U.S. Pat. Nos. 5,596,051 and 5,292,835), Matson (U.S. Pat. No. 3,516,941), Chao (U.S. Pat. No. 6,375,872), Foris et al. (U.S. Pat. Nos. 4,001,140; 4,087,376; 4,089,802 and 4,100,103), Greene et al. (U.S. Pat. Nos. 2,800,458; 2,800,457 and 2,730,456), Clark (U.S. Pat. No. 6,531,156), Saeki et al. (U.S. Pat. Nos. 4,251,386 and 4,356,109), Hoshi et al. (U.S. Pat. No. 4,221,710), Hayford (U.S. Pat. No. 4,444,699), Hasler et al. (U.S. Pat. No. 5,105,823), Stevens (U.S. Pat. No. 4,197,346), Riecke (U.S. Pat. No. 4,622,267), Greiner et al. (U.S. Pat. No. 4,547,429), and Tice et al. (U.S. Pat. No. 5,407,609), among others and as taught by Herbig in the chapter entitled "Microencapsulation" in Kirk-Othmer Encyclopedia of Chemical Technology, V.16, pages 438-463.

Other useful methods for microcapsule manufacture are: Foris et al., U.S. Pat. Nos. 4,001,140 and 4,089,802 describing a reaction between urea and formaldehyde; Foris et al., U.S. Pat. No. 4,100,103 describing reaction between melamine and formaldehyde; and British Pat. No. 2,062,570 describing a process for producing microcapsules having walls produced by polymerization of melamine and formaldehyde in the presence of a styrenesulfonic acid. Forming microcapsules from urea-formaldehyde resin and/or melamine formaldehyde resin is disclosed in U.S. Pat. Nos. Foris et al., 4,001,140; Foris et al., 4,089,802; Foris et al., 4,100,103; Foris et al., 4,105,823; and Hayford, 4,444,699. Alkyl acrylate-acrylic acid copolymer capsules are taught in Brown et al., U.S. Pat. No. 4,552,811. Each patent described throughout this application is incorporated herein by reference to the extent each provides guidance regarding microencapsulation processes and materials.

Interfacial polymerization is a process wherein a microcapsule wall or polyamide, an epoxy resin, a polyurethane, a polyurea or the like is formed at an interface between two phases. Riecke, U.S. Pat. No. 4,622,267 discloses an interfacial polymerization technique for preparation of microcapsules. The core material is initially dissolved in a solvent and an aliphatic diisocyanate soluble in the solvent mixture is added. Subsequently, a nonsolvent for the aliphatic diisocyanate is added until the turbidity point is just barely reached. This organic phase is then emulsified in an aqueous solution, and a reactive amine is added to the aqueous phase. The amine diffuses to the interface, where it reacts with the diisocyanate to form polymeric polyurethane shells. A similar technique, used to encapsulate salts which are sparingly soluble in water in polyurethane shells, is disclosed in Greiner et al., U.S. Pat. No. 4,547,429. Matson, U.S. Pat. No. 3,516,941 teaches polymerization reactions in which the material to be encapsulated, or core material, is dissolved in an organic, hydrophobic oil phase which is dispersed in an aqueous phase. The aqueous phase has dissolved materials forming aminoplast (amine and aldehyde) resin which upon polymerization form the wall of the microcapsule. A dispersion of fine oil droplets is prepared using high shear agitation. Addition of an acid catalyst initiates the polycondensation forming the aminoplast resin within the aqueous phase, resulting in the formation of an aminoplast polymer which is insoluble in both phases. As the polymerization advances, the aminoplast polymer separates from the aqueous phase and deposits on the surface of the dispersed droplets of the oil phase to form a capsule wall at the interface of the two phases, thus encapsulating the core material. Urea-formaldehyde (UF), urea-resorcinol-formaldehyde (URF), urea-melamine-formaldehyde (UMF), and melamine-formaldehyde (MF), capsule formations proceed in a like manner. In interfacial polymerization, the materials to form the capsule wall are in separate phases, one in an aqueous phase and the other in an oil phase. Polymerization occurs at the phase boundary. Thus, a polymeric capsule shell wall forms at the interface of the two phases thereby encapsulating the core material. Wall formation of polyester, polyamide, and polyurea capsules also typically proceed via interfacial polymerization.

Jahns, U.S. Pat. No. 5,292,835 teaches polymerizing esters of acrylic acid or methacrylic acid with polyfunctional monomers. Specifically illustrated are reactions of polyvinylpyrrolidone with acrylates such as butanediol diacrylate or methyl(meth)acrylate together with a free radical initiator.

Common microencapsulation processes can be viewed as a series of steps. First, the core material which is to be encapsulated is typically emulsified or dispersed in a suitable dispersion medium. This medium is typically aqueous but involves the formation of a polymer rich phase. Most frequently, this medium is a solution of the intended capsule wall material. The solvent characteristics of the medium are changed such as to cause phase separation of the wall material. The wall material is thereby contained in a liquid phase which is also dispersed in the same medium as the intended capsule core material. The liquid wall material phase deposits itself as a continuous coating about the dispersed droplets of the internal phase or capsule core material. The wall material is then solidified. This process is commonly known as coacervation.

Jabs et al., U.S. Pat. No. 4,847,152 teaches microcapsules with polyurea walls. The wall is the reaction product of an aromatic isocyanate with an isocyanate reactive group. The isocyanate reactive group can include di- and polyamines such as N-hydroxyethylethylenediamine, ethylene-1,2-diamine.

Hotz et al., U.S. Pat. Pub. 2013/0089590 teaches a fragrance microcapsule with a polyurea wall. The shell in the reaction product of at least two difunctional isocyanates and a difunctional amine.

EP 1693104 Maruyyama discloses microcapsules having a polyurethane or polyurea wall obtained from polycondensation of a polyfunctional isocyanate with a polyfunctional amine.

Schwantes, U.S. Pat. Pub. 2009/0274905 teaches cationic microcapsule particles where the wall in the reaction product of an amine acrylate with a multifunctional methacrylate in the presence of an acid and initiator; or alternatively an acid acrylate and multifunctional (meth)acrylate in the presence of a base and initiator.

A need has existed in the art for (meth)acrylate microcapsules which retain capsule contents over time, or until fractured or otherwise made permeable. A need has existed in the art in particular for (meth)acrylate microcapsules which have improved adherence to substrates.

U.S. Pat. No. 8,765,659 describes microcapsules coated with chitosan, polyvinyl acetal, polyvinyl alcohol, polyvinyl pyrrolidone/dimethyl aminoethyl methacrylate (PVP/DMAEMA) and other surface coatings.

U.S. Pat. Pub. 2016/0058678 describes use of deposition aids such as polyamine, polyvinyl pyrrolidone, poly(propylone) maleic anhydride, polyvinyl formamide and polyallyl amines.

A need exists for improved microcapsules which can adhere to surfaces without, or with reduced amounts of, deposition aid. The above references do not teach that an improved microcapsule can be achieved comprising a polysaccharide such as chitosan and (meth)acrylate wall material which can reduce or even obviate the need for a deposition aid. The microcapsules of the invention are useful in a variety of challenging environments, such as use with fabric enhancers, laundry, phase change and other industrial and commercial applications.

Definition

As used herein, reference to the term "(meth)acrylate" or "(meth)acrylic" is to be understood as referring to both the acrylate and the methacrylate versions of the specified monomer, oligomer, prepolymer and/or including the polymers thereof (for example "allyl (meth)acrylate" indicates that both allyl methacrylate and allyl acrylate are possible, similarly reference to alkyl esters of (meth)acrylic acid indicates that both alkyl esters of acrylic acid and alkyl esters of methacrylic acid are possible, similarly poly(meth)acrylate indicates that both polyacrylate and polymethacrylate are possible). Each alkyl moiety herein, unless otherwise indicated, can be from $C_1$ to $C_8$, or even from $C_1$ to $C_{24}$. References to (meth)acrylate materials are intended to encompass a broad spectrum of polymeric materials including, for example, poly(meth)acrylates, polyester poly(meth)acrylates, urethane and polyurethane poly(meth)acrylates (especially those prepared by the reaction of an hydroxyalkyl (meth)acrylate with a polyisocyanate or a urethane polyisocyanate), methylcyanoacrylate, ethylcyanoacrylate, diethyleneglycol di(meth)acrylate, trimethylolpropane tri(meth)acrylate, ethylene glycol di(meth)acrylate, allyl (meth)acrylate, glycidyl (meth)acrylate, (meth)acrylate functional silicones, di-, tri- and tetraethylene glycol di(meth)acrylate, dipropylene glycol di(meth)acrylate, polyethylene glycol di(meth)acrylate, di(pentamethylene glycol) di(meth)acrylate, ethylene di(meth)acrylate, neopentyl glycol di(meth)acrylate, trimethylolpropane tri(meth)acrylate, ethoxylated bisphenol A di(meth)acrylates, bisphenol A di(meth)acrylates, diglycerol di(meth)acrylate, tetraethylene glycol dichloroacrylate, 1,3-butanediol di(meth)acrylate, neopentyl di(meth)acrylate, trimethylolpropane tri(meth)acrylate, polyethylene glycol di(meth)acrylate and dipropylene glycol di(meth)acrylate and various multifunctional (meth)acrylates and multifunctional amine (meth)acrylates. Monofunctional acrylates, i.e., those containing only one acrylate group, may also be advantageously used. Typical monoacrylates include 2-ethylhexyl (meth)acrylate, 2-hydroxyethyl (meth)acrylate, cyanoethyl (meth)acrylate, 2-hydroxypropyl (meth)acrylate, p-dimethylaminoethyl (meth)acrylate, lauryl (meth)acrylate, cyclohexyl (meth)acrylate, tetrahydrofurfuryl (meth)acrylate, chlorobenzyl (meth)acrylate, aminoalkyl(meth)acrylate, various alkyl(meth)acrylates and glycidyl (meth)acrylate. Of course, mixtures of (meth)acrylates or their derivatives as well as combinations of one or more (meth)acrylate monomers, oligomers and/or prepolymers or their derivatives with other copolymerizable monomers, including acrylonitriles and methacrylonitriles may be used as well.

SUMMARY OF THE INVENTION

The present invention comprises a microcapsule comprising a core, and a shell surrounding the core material. The microcapsule made by the process taught in the invention incorporates chitosan into the microcapsule wall material. By chitosan incorporation into the wall material the microcapsules adhere to surfaces without or with reduced deposition aid.

In one aspect the invention teaches a population of microcapsules comprising a core material surrounded by a wall material comprising the reaction product of a polysaccharide having pendant amine groups reactive with an initiator of formula 1 and at least one multifunctional (meth)acrylate monomer free radically polymerized with the initiator of formula 1

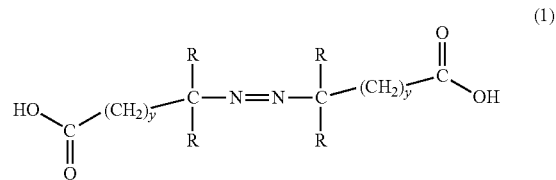

wherein each R is independently selected from hydrogen, $C_1$ to $C_8$ alkyl, or a cyano group; wherein each y is independently an integer from 1 to 8. When dispersed into an aqueous medium, a slurry can be formed greater than zero when measured at a pH of 5. Greater than zero in this context means the zeta potential is a more positive value.

In a further aspect the polysaccharide is chitosan. The chitosan can have a degree of deacetylation of at least 50%. Also, desirably the wall material comprises greater than 50 wt % of multifunctional (meth)acrylate. The multifunctional (meth)acrylate can be selected from the group consisting of mono-, di-, tri-, tetra-, penta-, hexa-, hepta-, or octa-functional acrylate or methacrylate esters, multi-functional urethane acrylate or methacrylate esters, and epoxy acrylates or methacrylates. The wall of material of the microcapsule can comprise from 0.1% to 20% by weight of the polysaccharide. In one embodiment the wall material comprises a polymer obtained by polymerization of 0.1% to 80% be weight of multifunctional (meth)acrylate monomer, 0.1% to 60% by weight of the polysaccharide and 0.1% to 30% by weight of the initiator of formula 1. Optionally, the population of microcapsules can comprise in addition an aqueous medium into which the microcapsules are dispersed forming a slurry, said slurry having a zeta potential greater than zero millivolts when measured at a pH of 5.

Disclosed also is a process of forming a population of microcapsules comprising a core material, and a wall material surrounding the core material, the wall material comprising the reaction product of a polysaccharide having one or more amine groups, and a multifunctional (meth)acrylate monomer, the microcapsule population formed by providing a water phase comprising a polysaccharide having a pendant amine group and a first initiator of formula 1,

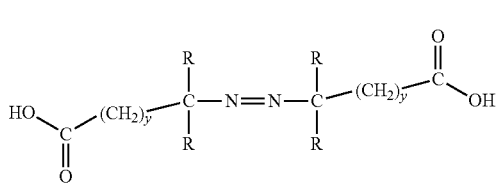
(1)

wherein each R is independently selected from hydrogen, $C_1$ to $C_8$ alkyl, or a cyano group; wherein each y is independently an integer from 1 to 8, the first initiator having a carboxyl functional group and a free radical azonitrile moiety; providing an oil phase and dispersing or dissolving a core material into the oil phase; dispersing a multifunctional (meth)acrylate monomer, and optionally a second initiator, into the oil phase; combining the oil phase with the water phase; and heating or exposing to actinic radiation the combined oil phase and water phase, to activate the initiator or initiators such as of the water phase to generate free radicals thereby polymerizing the multifunctional methacrylate monomer, and in addition adjusting the pH such that the carboxyl functional group of the first initiator reacts with the amine groups of the polysaccharide.

The process also comprises forming a population of microcapsules comprising a core material, chitosan and a (meth)acrylate wall material surrounding the core material, the microcapsule population being formed by providing a benefit agent core material comprising an oil soluble fluid material or oil-dispersible solid particle dispersed in an oil soluble fluid material; providing an oil internal phase comprising a diluent; dividing the oil internal phase into oil 1 and oil 2; dispersing an initiator into oil 1; dispersing into oil 2 a multifunctional (meth)acrylate monomer or oligomer, and optimally one or more acrylates selected from the group consisting of monofunctional acrylates, difunctional (meth) acrylate esters and polyfunctional (meth)acrylate esters, and dispersing into oil 2 the oil soluble fluid core material or oil-dispersible solid particle dispersed in a fluid core material; heating or exposing the initiator, oils or combined oils 1 and 2 to actinic radiation sufficient to activate the initiator of oil 1; combining oil 1 and oil 2 forming a combined oil continuous internal phase and allowing reaction to proceed for a time sufficient to pre-polymerize the multifunctional monomers or oligomers of or from oil 2; providing a water phase comprising chitosan and a water soluble or dispersible initiator of formula 1

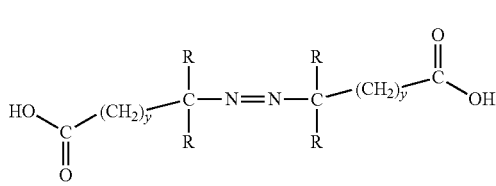
(1)

herein each R is independently selected from hydrogen, $C_1$ to $C_8$ alkyl, or a cyano group; wherein each y is independently an integer from 1 to 8; heating or exposing the combined oils to actinic radiation sufficiently to activate the initiator of the water phase; forming a chitosan and (meth) acrylate mixture by dispersing the combined oil internal phase into the water phase; emulsifying the chitosan and (meth)acrylate mixture by subjecting the mixture to high shear agitation; heating or exposing to actinic radiation the chitosan and (meth)acrylate mixture for a time and temperature sufficient whereby the multifunctional (meth)acrylate and chitosan bond and migrate to the interface of the oil and water phases thereby surrounding the core material in the oil phase and forming wall material.

The initiator according to formula 1, in certain embodiments, is 4,4'-azobis (4-cyanopentanoic acid), and the chitosan can have a degree of deacetylation of at least 75%. In certain embodiments the microcapsule wall can contain from 0.01% to 14% by weight of chitosan. Alternatively, the chitosan is partially deacetylated. The chitosan can be a D, L lactic acid chitosan, or a glycolic acid chitosan, or the chitosan can be selected from the group of water soluble chitosans selected from glycerol chitosan, hydrolyzed chitosan, n-hydroxypropyl chitosan, polyoxyalkylene chitosan, and chitosan oligosaccharide. The chitosan can even be comprised of D-glucosamine and N-acetyl glucosamine moieties, and the ratio of D-glucosamine to N-acetyl glucosamine is typically 3:1 or greater, or even 6:1 or 10:1.

In one embodiment the oil internal phase is isopropyl myristate. The core material can be selected from a biological active, a dye, a perfume, a fragrance, a phase change material, a lubricant or a chromogen, and the multifunctional (meth)acrylate can be selected from the group consisting of mono-, di-, tri-, tetra-, penta-, hexa-, hepta-, or octa-functional acrylate or methacrylate esters, multi-functional urethane acrylate or methacrylate esters, and epoxy acrylates or methacrylates.

The present invention in another aspect discloses an improved microcapsule and a process for forming a population of microcapsules comprising a core material and a chitosan and acrylate wall material surrounding the core material, the microcapsule population being formed by the steps of:

i) providing an oil soluble fluid core material or oil-dispersible solid particle dispersed in a fluid core material;

ii) providing an oil internal phase comprising a diluent such as selected from esters of glycerol and fatty acids wherein at least one of the fatty acids is $C_{12}$ or greater, iii) dividing the oil internal phase into oil 1 and oil 2;

iv) dispersing into oil 1 an initiator;

v) dispersing into oil 2 a multifunctional acrylate or methacrylate monomer or oligomer, substantially free of amine, and dispersing into oil 2 the oil soluble fluid core material or oil-dispersible solid particle dispersed in a fluid core material;

vi) heating or exposing to actinic radiation sufficiently to activate the initiator of oil 1 vii) combining oil 1 and oil 2 forming a combined oil continuous internal phase and allowing reaction to proceed for a time sufficient to pre-polymerize the multifunctional monomers or oligomers from oil 2;

viii) providing a water phase comprising chitosan and a water soluble or dispersible initiator of formula 1

Formula 1

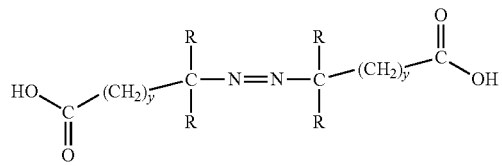

wherein each R is independently selected from hydrogen, $C_1$ to $C_8$ alkyl, or a cyano group; wherein each y is independently an integer from 1 to 8;

ix) heating or exposing to actinic radiation sufficiently to activate the initiator of the water phase x) forming a chitosan-acrylate mixture by dispersing the combined oil internal phase into the water phase;

xi) emulsifying the chitosan-acrylate mixture by subjecting the mixture to high shear agitation; and heating or exposing to actinic radiation the chitosan-acrylate mixture for a time and temperature sufficient whereby the multifunctional acrylate or methacrylate and chitosan bond and migrate to the interface of the oil and water phases thereby surrounding the core material in the oil phase and forming wall material. The bonding can be physical entanglement, hydrogen bonding or chemical bond formation.

DETAILED DESCRIPTION

The invention teaches a population of microcapsules comprising a core material surrounded by a wall material comprising the reaction product of a polysaccharide having amine groups reactive with an initiator of formula 1 and at least one multifunctional (meth)acrylate monomer free radically polymerized with the initiator of formula 1

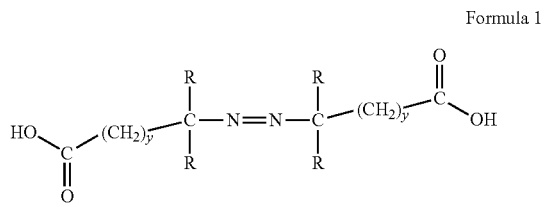

Formula 1 wherein each R is independently selected from hydrogen, $C_1$ to $C_8$ alkyl, or a cyano group; wherein each y is independently an integer from 1 to 8.

In one aspect the polysaccharide is chitosan, and preferably with a degree of deacetylation ("DDA") of at least 50%, and preferably at least 75%. Chitosan, for purposes of the invention, can be a glycolic acid chitosan, including D, L lactic acid chitosan, derivatives such as water soluble chitosans selected, for purposes of illustration and not limitation, from glycerol chitosan, hydrolyzed chitosan, N-cinnamoyl chitosan, chitosan crosslinked with tripolyphoshate, N-hydroxypropyl chitosan, polyoxyalkylene chitosan, and chitosan oligosaccharide. Preferably chitosan is comprised of N-acetyl glucosamine moieties, and the ratio of D-glucosamine to N-acetyl glucosamine is 3:1 or greater. The multifunctional (meth)acrylate of the wall material can be an am inoalkyl(meth)acrylate or an am inoalkyl(meth)acrylamide. The wall material comprises the reaction product of a polysaccharide having one or more amine groups, and a multifunctional (meth)acrylate monomer, wherein the microcapsule population is formed by providing a water phase comprising a polysaccharide and a first initiator of formula 1, the first initiator having a carboxyl functional group and a free radical azonitrile moiety; providing an oil phase and dispersing or dissolving a core material into the oil phase; dispersing a multifunctional (meth)acrylate monomer, and optionally a second initiator, into the oil phase; combining the oil phase with the water phase; and heating or exposing to actinic radiation the combined oil phase and water phase, to activate the initiator of the water phase to generate free radicals and to polymerize the multifunctional methacrylate monomer, and adjusting the pH such that the carboxyl functional group of the first initiator reacts with the amine groups of the polysaccharide.

The microcapsules are of core shell type. In one embodiment, the microencapsulation involves oil in water emulsification and optionally can involve the use of a divided oil phase to facilitate encapsulation. The microcapsules comprise an oil soluble or dispersible benefit agent core material and a shell surrounding the benefit agent core material.

The shell is the reaction product of the polysaccharide such as chitosan with the carboxyl substituted initiators of formula 1.

The amino groups of chitosan react, for example, with the initiator 4,4'-azobis(4-cyanopentanoic acid), and involves reaction of the amine group of chitosan with one of the terminal carboxylate groups of the initiator forming amidic carboxyl linkages between the molecules.

The initiator surprisingly serves a dual function of solubilizing chitosan and also as a reactant in wall formation. As the initiator continues to provide free radicals, reaction of the (meth)acrylate monomers also proceeds further, forming wall material at the water oil interphase.

This reaction of chitosan with the free radical generating initiator having carboxyl functional groups and azonitrile proceeds by disassociation of the initiator. The carboxyl formation can react with the chitosan amine and the free radical azonitrile portion of the initiator furthering free radical polymerization of (meth)acrylate monomers.

The invention can be usefully adapted for use with acrylate microencapsulation processes such as the free radical initiator promoted reaction of aminoalkyl(meth)acrylate with multifunction (meth)acrylates such as taught in Schwantes U.S. Pat. No. 8,071,214 incorporated herein by reference.

The invention is useful with acrylate formation processes such as the acrylate encapsulation taught by Schwantes US published application 2014 0186630 and U.S. Pat. No. 6,592,900.

The invention can also be applied with (meth)acrylates such as aminoalkyl(meth)acrylate and aminoalkyl(meth)acrylamides. Aminoalkylacrylates and aminalkylacrylamides are illustrated in U.S. Pat. No. 6,849,591 and may be usefully applied with the reaction product of polysaccharide and the initiator of formula 1 to form chitosan modified (meth)acrylate wall material in microcapsules.

In the invention, the shell comprises the reaction product of the polysaccharide such as chitosan and a multifunctional (meth)acrylate monomer or oligomer.

The invention improves upon the prior art processes by incorporation of a polysaccharide having pendant amine groups into a reaction of a multifunctional (meth)acrylate monomer free radically polymerized with an initiator having carboxy functionality. "Monomers" herein are understood as inclusive of oligomers. The polysaccharide having pendant amine groups participates in the formation of the microcapsule wall material.

Through selection of the polysaccharide having pendant amine groups, the resulting shell or microcapsule wall can be adjusted as to desired cationic character where an adherent microcapsule for anionic surfaces and textures is useful for the intended end use application.

The proportion of the polysaccharide having pendant amine groups to total monomer of the capsule wall or shell desirably ranges from 1:20 to 1:7. In alternative useful embodiments the proportion of polysaccharide to total monomer is 45% or less, 40% or less, preferably 35% or less, or even 30% or less, or even 10% or less, or 5% or less, or even 3% or less. 0.01 to 14% or even 5% to 14% by weight is a preferred range, particularly for chitosan having pendant amine groups, the comparison being to total monomer of the capsule wall.

The balance of the capsule wall primarily is the reaction product of the multifunctional (meth)acrylate and free radical initiator of formula 1, along with any optional monofunctional (meth)acrylates.

In useful embodiments, the multifunctional (meth)acrylate comprises the major component of the shell.

The polysaccharide imparts zeta potential values to the shell, and even substantially positive zeta potentials are shown in Table 2. As shown in Table 2, the zeta potential of microcapsules according to the invention, when formed into aqueous slurries, is greater than 0 millivolts, or even greater than 14 millivolts or even greater than 25 millivolts. Zeta potential of the slurry is measured at pH of about 5.

Multifunctional (meth)acrylate monomers or oligomers are defined for purposes hereof to be multifunctional or methacrylate monomers or oligomers and include, by way of illustration and not limitation, mono-; di-; tri-; tetra- penta-; hexa-; hepta-; or octa-functional acrylate esters, methacrylate esters and multi-functional polyurethane acrylate esters and epoxy acrylates. Monomers shall be understood as including oligomers thereof.

Useful multifunctional (meth)acrylate monomers in the invention are one or more di- and poly-functional acrylate esters, difunctional (meth)acrylate esters, polyfunctional (meth)acrylate esters, difunctional urethane acrylate esters, polyfunctional urethane acrylate esters and polyfunctional and difunctional epoxy acrylate monomers and oligomers used alone or in combination as blends. In alternate embodiments, optionally, the di- and polyfunctional acrylates, methacrylates, urethane acrylates, and epoxy acrylates are further blended with monofunctional acrylates, methacrylates, urethane acrylates and epoxy acrylates.

In an aspect of the invention multi-functional acrylate or methacrylate monomers or oligomers preferably are selected to have a Tg>60° C., in one aspect greater than 70° C., and in another aspect greater than 80° C., and can include by way of illustration and not limitation, allyl methacrylate; triethylene glycol dimethacrylate; ethylene glycol dimethacrylate, diethylene glycol dimethacrylate, aliphatic or aromatic polyfunctional (meth)acrylates such as multifunctional urethane acrylates, urethane diacrylates, hexafunctional urethane acrylates, difunctional urethane acrylates, ethoxylated aliphatic difunctional urethane methacrylates, aliphatic or aromatic urethane dimethacrylates, epoxy acrylates, epoxymethacrylates; tetraethylene glycol dimethacrylate; polyethylene glycol dimethacrylate; 1,3 butylene glycol diacrylate; 1,4-butanediol dimethacrylate; 1,4-butaneidiol diacrylate; diethylene glycol diacrylate; 1,6 hexanediol diacrylate; 1,6 hexanediol dimethacrylate; neopentyl glycol diacrylate; polyethylene glycol diacrylate; tetraethylene glycol diacrylate; triethylene glycol diacrylate; 1,3 butylene glycol dimethacrylate; tripropylene glycol diacrylate; ethoxylated bisphenol diacrylate; ethoxylated bisphenol dimethylacrylate; dipropylene glycol diacrylate; alkoxylated hexanediol diacrylate; alkoxylated cyclohexane dimethanol diacrylate; propoxylated neopentyl glycol diacrylate, trimethylolpropane trimethacrylate; trimethylolpropane triacrylate, pentaerythritol triacrylate, ethoxylated trimethylolpropane triacrylate, propoxylated trimethylolpropane triacrylate, propoxylated glyceryl triacrylate, ditrimethylolpropane tetraacrylate, dipentaerythritol pentaacrylate and ethoxylated pentaerythritol tetraacrylate, or blends of any of the foregoing.

Crosslinking may be effected via groups capable of addition or condensation.

Excluding solvent, the multi-functional acrylate or methacrylate monomers are used in a relative ratio of from about 99.9:0.1 to about 10:90, preferably from about 99.5:0.5 to about 3:97, and even 99:1 to about 2:98.

Monofunctional acrylates, i.e., those containing only one acrylate group, may also be included in the oil phase. Typical monoacrylates include 2-ethylhexyl (meth)acrylate, 2-hydroxyethyl (meth)acrylate, 2-hydroxypropyl (meth)acrylate, lauryl (meth)acrylate, cyclohexyl (meth)acrylate, tetrahydrofurfuryl (meth)acrylate, chlorobenzyl (meth)acrylate, and glycidyl (meth)acrylate. In some circumstances mixtures of mono or multi-functional (meth)acrylates or their derivatives as well as combinations of one or more (meth)acrylate monomers, oligomers and/or prepolymers or their derivatives with other copolymerizable monomers, may be useful as well. Optionally from 0 to 10% by weight of the oil phase is a monofunctional acrylate or methacrylate monomer or oligomer.

For example, in the process of making the capsules, assuming a system of about 800 grams with solvent, the largest constituents are typically solvent, 10 to 70 weight percent, preferably 25 to 55 weight percent oil phase solvent and oil; 10 to 70 weight percent, preferably 35 to 65 weight percent water; 40 to 99.5 weight percent, or even 86 to 95 weight percent, or even 50 to 99.5 weight percent of multi-functional acrylate or methacrylate monomer or oligomer; oil up to 20 weight percent. Initiator is 10% or less, usually about 5% or less, preferably 2% by weight or less and more preferably 1% or less. The ratio by weight of the water phase initiator to multifunctional acrylate is from 0.1:99.9 parts to 20:80 by weight; preferably from 0.1:99.9 to about 10:90 parts by weight, or even from 0.2 to about 5:95 parts by weight.

In one aspect of the process of the invention, the benefit agent core material is oil soluble fluid core material or oil dispersible solid particles dispersed in a fluid core material.

The oil soluble fluid core material can be the same as the internal phase oil or optionally different internal phase oil material. The oil soluble fluid material can optimally be the benefit agent core material itself.

An internal phase oil is provided. The internal phase oil can comprise various diluents. In a useful embodiment, the internal phase oil is an ester of glycerol and fatty acids wherein at least one of the fatty acids is $C_{12}$ or greater.

The oil internal phase is divided into an oil 1 and an oil 2. An initiator is dispersed into oil 1. Initiators are described more fully herein. A separate water phase is also used and an initiator in the water phase as per formula 1.

A water phase is provided comprising water, chitosan and a water soluble or dispersible initiator of formula 1

Formula 1

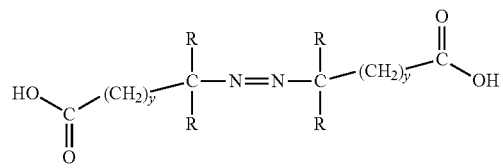

wherein each R is independently selected from hydrogen, $C_1$ to $C_8$ alkyl, or a cyano group; wherein each y is independently an integer from 1 to 8.

Compounds according to formula 1 include 4,4'-azobis (4-cyanopentanecarboxylic) acid, also known as 4,4'-azobis (4-cyanovaleric acid); 4,4'-azobis(4-cyanohexanoic acid); 4,4'-azobis(5-cyanohexanoic acid); 4,4'-azobis(pentanoic acid); and 4,4'-azobis(4-methylpentanoic acid);

In one aspect a multifunctional (meth)acrylate monomer or oligomer substantially free of amine is dispersed into oil 2. The benefit agent core material, which can be an oil soluble fluid core material or an oil dispersible solid particle dispersed in the fluid core material, is also dispersed into oil 2. Optionally the oil soluble fluid core material can be the same or similar to the oil 2 material.

Oil 1 can be selected from the same or similar materials as oil 2.

The shell is the reaction product of chitosan and the multifunctional (meth)acrylate.

Chitosan is soluble in acidic solution such as hydrochloric acid, lactic acid, propionic acid, succinic acid, acetic acid, citric acid and phosphoric acid, but generally insoluble in water above pH 7. At pH values below 4, the amino groups of chitosan promote electrostatic repulsion and the polymer swells. In acid solution the free amine groups are believed to from hydrogen bonds with adjacent oxygen groups. Chitosan is a cationic polysaccharide at pH below about 6.5.

The dissolved polysaccharide has positive charged $-NH_3+$ groups and adheres to anionic surfaces. Chitosan forms aggregate with polyanions and chelates heavy metals.

Solubility of chitosan in aqueous solution can be increased by modification of the chitosan with succinic acid or succinic anhydride, for example, o-succinyl-chitosan, or by quaternization, and/or carboxymethylation. Derivatives such as hydroxypropyl chitosan or substitution with phosphorus or alkyl groups are known to increase solubility in water. Phosphoric and alkyl substitution can introduce hydrophilic and hydrophobic groups or segments that can be used to tailor solubility and stabilize emulsions.

Chitosan is a heteropolymer of N-acetyl glucosamine and D-glucosamine. Chitosan is a deacetylated from of chitin. Chitosan is a polysaccharide and is basic.

Chitosan can be characterized by degree of deacetylation and molecular weight. The molecular weight of chitosan can range from 50 to 2000 kDa. In one aspect the molecular weight of the chitosan is at least 3 kDa, or even at least 50 kDa, to 1000 kDa or even to 2000 kDa.

Useful in the process of the invention is chitosan at least 50% deacetylated, or even at least 65% deacetylated or even at least 75% deacetylated. In another aspect, the degree of deacetylation is from 50% to 100%, from 70% to 100%, from 75% to 100%, from 60% to 90%, from 50% to 100%, or even from 25% to 70%, from 25% to 98%, from 30% to 98% or even from 50% to 98% deacetylated. In one aspect polyglucosamine is also useful.

Chitin can be deacetylated by treatment with alkali and heated to remove acetyl groups from chitin. For example, a 40% NaOH solution at temperatures above 110° C. can form a cationic chitosan.

In one aspect, the ratio of D-glucosamine to N-acetyl glucosamine 3:1 or greater, or even is from 1:4 to 4:1, or even from 1:4 to 1:1, or even from 1:4 to 1:0.

The extent of deacetylation tends to be a function of alkali concentration, temperature and time, with increasing deacetylation at elevated temperatures and increasing alkali, such as NaOH, concentration. With concentrated acids, poly D-glucosamine can be formed. Molecular weight of the chitosan can be decreased through increasing the duration of the deacetylation processing.

Deacetylation removes acetyl groups leaving $-NH_2$ groups. In one aspect the chitosan usefully has from 0 to 0.3 fraction of N-acetyl units.

The shell surrounding the core material is a reaction product of a chitosan and (meth)acrylate material, an optimally one or more monofunctional acrylate or difunctional or polyfunctional (meth)acrylate esters. The two materials can be a reaction product of hydrogen bonded, complex coacervated or the result of ionic interaction and either physically cross-linked or chemically cross-linked. While not being limited to theory, the shell is believed to be largely a physical cross-linking of the chitosan and multi-functional (meth)acrylate, and optionally includes additional (meth) acrylate esters and/or monofunctional acrylates.

The acid group of the initiator of formula 1 reacts with the amine group of the chitosan forming an ionic bond. The cross-linking of the acid group of the initiator with the amine group of the chitosan results in deposition of the polymerized chitosan and initiator onto the forming capsule wall material, resulting in incorporation of chitosan chemically into the microcapsule wall. The free radical portion of the initiator promotes polymerization of the (meth)acrylate monomer forming the capsule wall.

Multifunctional (meth)acrylate monomers or oligomers can include mono-; di-; tri-; tetra- penta-; hexa-; hepta-; or octa-functional acrylate esters, methacrylate esters and multi-functional polyurethane acrylate esters and epoxy acrylates. Monomers shall be understood as including oligomers thereof. Optionally, an inhibitor such as hydroquinone can be added to the monomer and initiator blend in the capsules to prevent premature polymerization.

Useful in the invention are various multifunctional (meth) acrylate monomers such as di- and poly-functional (meth) acrylate esters, difunctional (meth)acrylate esters, polyfunctional (meth)acrylate esters, difunctional urethane acrylate esters, polyfunctional urethane acrylate esters and polyfunctional and difunctional epoxy acrylate monomers and oligomers used alone or in combination as blends. In alternate embodiments, optionally, the di- and polyfunctional acrylates, methacrylates, urethane acrylates, and epoxy amine acrylates are further blended with monofunctional acrylates, methacrylates, urethane acrylates and epoxy acrylates.

Monofunctional acrylates, i.e., those containing only one acrylate group, may also be included in the oil phase. Typical monoacrylates include 2-ethylhexyl(meth)acrylate, 2-hydroxyethyl(meth)acrylate, 2-hydroxypropyl(meth)acrylate, lauryl(meth)acrylate, cyclohexyl(meth)acrylate, tetrahydrofurfuryl(meth)acrylate, chlorobenzyl(meth)acrylate, and glycidyl(meth)acrylate. In some circumstances mixtures of mono or multi-functional (meth)acrylates or their derivatives, as well as combinations of one or more (meth)acrylate monomers, oligomers and/or prepolymers or their derivatives with other nonpolymerizable monomers, may be useful as well. Preferably from 0 to 10% by weight of the oil phase is a monofunctional acrylate or methacrylate monomer or oligomer.

For example, in the process of making capsules, assuming a system of about 80 grams with solvent, the largest constituents are typically solvent, 10 to 70 weight percent, preferably 25 to 55 weight percent oil phase solvent and oil; 10 to 70 weight percent, preferably 35 to 65 weight percent water; 0.01 to 1 weight percent, preferably 0.1 to 10 weight percent, usually 0.5 to 8 weight percent multi-functional acrylate or methacrylate monomer or oligomer; oil to 20 weight percent. Initiator is 10% or less, usually about 5% or less, preferably 2% by weight or less and more preferably 1% or less. The ratio by weight of the water phase initiator to multifunctional acrylate is from 0.1:99.9 parts to 10:80 by weight, preferably from 0.1:99.9 to about 10:90 parts by weight, or even from 0.2:99.9 to about 5:98 parts by weight If desired the microcapsules can be separated from the aqueous medium. The slurry can either be used as is, used as a dewatered cake, or used in dry powder form depending on the application.

In certain embodiments initiators in addition to those of formula 1 can be incorporated in the oil or water phase. Initiators are energy activated and generate free radicals when subjected to heat or other energy input such as actinic radiation or ion beam. Second initiators can include peroxy initiators, azo initiators, peroxides, and compounds such as 2,2'-azobismethylbutyronitrile, dibenzoyl peroxide. More particularly, and without limitation the free radical initiator can be selected from the group of initiators comprising an azo or peroxy initiator, such as peroxide, dialkyl peroxide, alkyl peroxide, peroxyester, peroxycarbonate, peroxyketone and peroxydicarbonate, 2,2'-azobis (isobutylnitrile), 2,2'-azobis(2,4-dimethylpentanenitrile), 2,2'-azobis (2,4-dimethylvaleronitrile), 2,2'-azobis(2-methylpropanenitrile), 2,2'-azobis (methylbutyronitrile), 1,1'-azobis (cyclohexanecarbonitrile), 1,1'-azobis(cyanocyclohexane), benzoyl peroxide, decanoyl peroxide; lauroyl peroxide; benzoyl peroxide, di(n-propyl) peroxydicarbonate, di(sec-butyl) peroxydicarbonate, di(2-ethylhexyl) peroxydicarbonate, 1,1-dimethyl-3-hydroxybutyl peroxyneodecanoate, .alpha.-cumyl peroxyneoheptanoate, t-amyl peroxyneodecanoate, t-butyl peroxyneodecanoate, t-amyl peroxypivalate, t-butyl peroxypivalate, 2,5-dimethyl 2,5-di(2-ethylhexanoyl peroxy) hexane, t-amyl peroxy-2-ethyl-hexanoate, t-butyl peroxy-2-ethylhexanoate, t-butyl peroxyacetate, di-t-amyl peroxyacetate, t-butyl peroxide, di-t-amyl peroxide, 2,5-dimethyl-2,5-di-(t-butylperoxy)hexyne-3, cumene hydroperoxide, 1,1-di-(t-butylperoxy)-3,3,5-trimethyl-cyclohexane, 1,1-di-(t-butylperoxy)-cyclohexane, 1,1-di-(t-amylperoxy)-cyclohexane, ethyl-3,3-di-(t-butylperoxy)-butyrate, t-amyl perbenzoate, t-butyl perbenzoate, ethyl 3,3-di-(t-amylperoxy)-butyrate, and the like. Blends of initiators can also be employed. Initiators are available commercially, such as Vazo initiators, which typically indicate a decomposition temperature for the initiator. Preferably the initiator is selected to have a decomposition point of about 50° C. or higher. Usefully multiple initiators are employed, either as a blend in the oil phase, or in either of the oil or water phases. Preferably initiators are selected to stagger the decomposition temperatures at the various steps, pre-polymerization, wall formation and hardening or polymerizing of the capsule wall material. For example, a first initiator in the oil phase can decompose at 55° C., to promote prepolymer formation, a second can decompose at 60° C. to aid forming the wall material. Optionally a third initiator can decompose at 65° C. to facilitate polymerization of the capsule wall material. The total amount of initiator can be typically as low as 0.1 weight percent or as high as 10 weight percent.

The terms oil internal phase, internal phase oil and oil phase are synonymous for purposes hereof, and can comprise a diluent and can be selected from hydrocarbons, more particularly hydrocarbon solvents and the solvents can include by way of illustration and not limitation, ethyldiphenylmethane, butyl biphenyl ethane, benzylxylene, alkyl biphenyls such as propylbiphenyl and butylbiphenyl, dialkyl phthalates e.g. dibutyl phthalate, dioctylphthalate, dinonyl phthalate and ditridecylphthalate; 2,2,4-trimethyl-1,3-pentanediol diisobutyrate, alkyl benzenes such as dodecyl benzene; but also carboxylates, ethers, or ketones such as diaryl ethers, di(aralkyl)ethers and aryl aralkyl ethers, ethers such as diphenyl ether, dibenzyl ether and phenyl benzyl ether, liquid higher alkyl ketones (having at least 9 carbon atoms), alkyl or aralky benzoates, e.g., benzyl benzoate, alkylated naphthalenes such as dipropylnaphthalene, partially hydrogenated terphenyls; high-boiling straight or branched chain hydrocarbons, arenes and alkaryl hydrocarbons such as toluene, vegetable oils such as canola oil, soybean oil, coin oil, sunflower oil, or cottonseed oil, methyl esters of fatty acids derived from transesterification of canola oil, soybean oil, cottonseed oil, corn oil, sunflower oil, pine oil, lemon oil, olive oil, or methyl ester of oleic acid, vegetable oils, esters of vegetable oils, e.g. soybean methyl ester, straight chain saturated paraffinic aliphatic hydrocarbons of from 10 to 13 carbons; $C_8$-$C_{42}$ esters, esters of glycerol, fatty acids where at least one of the fatty acids is $C_{12}$ or greater, ethyl hexanoate, methyl heptanoate, butyl butyrate, methyl benzoate, methyl such as nonoate, methyl decanoate, methyl dodecanoate, methyl octanoate, methyl laurate, methyl myristate, methyl palmitate, methyl stearate, ethyl heptanoate, ethyl octanoate, ethyl nonoate, ethyl decanoate, ethyl dodecanoate, ethyl laurate, ethyl myristate, ethyl palmitate, ethyl stearate, isopropyl myristate, isopropyl palmitate, ethylhexyl palm itate, isoamyl laurate, butyl laurate, octyl octanoate, decyl decanoate, butyl stearate, lauryl laurate, stearyl palm itate, stearyl stearate, stearyl behenate, and behenyl behenate. Mixtures of the above can also be employed. Common diluents such as straight chain hydrocarbons can also be blended with the solvents, or blend of solvents. The solvent is selected on the basis of hydrophobicity and ability to disperse or solvate the multifunction (meth)acrylate monomer or oligomer and the intended benefit agent of the core material.

The capsules according to the invention are useful with a wide variety of capsule contents ("core materials"), commonly referred to as benefit agents, including, by way of illustration and without limitation, the internal phase oils, solvent oils, phase change materials, lubricants, dyes, perfumes, fragrances, cleaning oils, polishing oils, flavorants, nutrients, sweeteners, chromogens, pharmaceuticals, biological actives such as fertilizers, herbicides or pesticides, and the like. The microcapsule core materials can include materials which alter rheology or flow characteristics, or extend shelf life or product stability. Essential oils as core materials can include, for example, by way of illustration wintergreen oil, cinnamon oil, clove oil, lemon oil, lime oil, orange oil, peppermint oil and the like. Dyes can include fluorans, lactones, indolyl red, I6B, leuco dyes, all by way of illustration and not limitation. The core material typically should be dispersible or sufficiently soluble in the capsule internal phase material namely in the internal phase oil or soluble or dispersible in the monomers or oligomers solubilized or dispersed in the internal phase oil. The core materials are preferably liquid but can be solid depending on the materials selected, and with temperatures appropriately adjusted to effect dispersion.

An emulsion is formed by emulsifying under high shear agitation the oil or combined oils into the water phase. Optionally the water phase can also include emulsifiers. The water phase emulsifier can be selected form one or more of polyalkylene glycol ether, condensation products of alkyl phenols, aliphatic alcohols, or fatty acids with alkylene oxide, ethoxylated alkyl phenols, ethoxylated arylphenols, ethoxylated polyaryl phenols, carboxylic esters solubilized with a polyol, polyvinyl alcohol, polyvinyl acetate, or copolymers of polyvinyl alcohol polyvinyl acetate, polyacrylamide, poly(N-isopropylacrylamide), poly(2-hydroxypropyl methacrylate), poly(2-ethyl-2-oxazoline), poly(2-isopropenyl-2-oxazoline-co-methyl methacrylate), poly(methyl vinyl ether), and polyvinyl alcohol-co-ethylene). Especially useful polyvinyl alcohols include polyvinyl alcohols of molecular 13,000 to 1876,000 Daltons, preferably from 13,000 to about 23,000 Daltons, or even from 146,000 to 186,000 Daltons. The polyvinyl alcohol can be partially or fully hydrolyzed.

Polyvinyl alcohol partially hydrolyzed in the range of 85 to 95% hydrolyzed is preferred. Partially hydrolyzed polyvinyl alcohol at 88% hydrolysis or less was useful, with about 88% hydrolysis being more preferred.

The emulsion is heated in one or more steps to form a wall material comprising the reaction product of the multifunctional (meth)acrylate and chitosan, the wall surrounding the benefit agent core material.

Optionally, deposition aids can be included, or applied as a coating in one or more layers over formed or forming microcapsules, to increase deposition or adhesion of the microcapsules to various surfaces such as various substrates including but not limited to paper, fabric skin, hair, towels, or other surfaces. Deposition aids can include poly (acrylamide-co-diallyldimethylammonium chloride, poly (diallyldimethylammonium chloride, polyethylenimine, cationic polyamine, poly [(3-methyl-1-vinylimidazolium chloride)-co-(1-vinylpyrrolidone)], copolymer of acrylic acid and diallyldimethylammonium chloride, cationic guar, guar gum, an organopolysiloxane such as described in US Publication 20150030557, incorporated herein by reference. In a further embodiment, the above-described microcapsules can comprise a deposition aid, and in a further aspect the deposition aid coats the outer surface of the shell of the microcapsule.

In a further aspect, in addition to the chitosan material incorporated into the microcapsule wall, a deposition aid in one or more layers on the microcapsules can be applied and can comprise a material selected from the group consisting of poly(meth)acrylate, poly(ethylene-maleic anhydride), polyamine, wax, polyvinylpyrrolidone, polyvinylpyrrolidone co-polymers, polyvinylpyrrolidone-ethyl acrylate, polyvinylpyrrolidone-vinyl acrylate, polyvinylpyrrolidone methylacrylate, polyvinylpyrrolidone-vinyl acetate, polyvinyl acetal, polyvinyl butyral, polysiloxane, poly(propylene maleic anhydride), maleic anhydride derivatives, co-polymers of maleic anhydride derivatives, polyvinyl alcohol, styrene-butadiene latex, gelatin, gum Arabic, carboxymethyl cellulose, carboxymethyl hydroxyethyl cellulose, hydroxyethyl cellulose, other modified celluloses, sodium alginate, chitosan, casein, pectin, modified starch, polyvinyl acetal, polyvinyl butyral, polyvinyl methyl ether/maleic anhydride, polyvinyl pyrrolidone and its co polymers, poly(vinyl pyrrolidone/methacrylamidopropyl trimethyl ammonium chloride), polyvinylpyrrolidone/vinyl acetate, polyvinyl pyrrolidone/dimethylaminoethyl methacrylate, polyvinyl amines, polyvinyl formamides, polyallyl amines and copolymers of polyvinyl amines, polyvinyl formamides, and polyallyl amines and mixtures thereof.

The size of the capsules can be controlled by adjusting the speed of agitation. Smaller size dispersions are achieved through faster agitation resulting in smaller capsules Emulsifying agents or protective colloids can be conveniently employed to facilitate dispersion. Such materials, for example, include carboxylated or partially hydrolyzed polyvinyl alcohol, methyl cellulose and various latex materials, stearates, lecithins and various surfactants.

The microcapsules according to the invention can be used to microencapsulate various core materials such as chromogens and dyes, flavorants, perfumes, sweeteners, fragrances, oils, fats, pigments, cleaning oils, lubricating oils, pharmaceuticals, pharmaceutical oils, perfume oils, mold inhibitors, antimicrobial agents, absorbers, adhesives, phase change materials, scents, fertilizers, nutrients and herbicides by way of illustration and without limitation.

Microencapsulation can facilitate processing by increasing particle size or by converting liquids into free-flowing solids. The largest volume application of microcapsules is in imaging systems such as carbonless papers.

The microcapsules are useful in a variety of challenging environments, such as use with fabric enhancers, laundry, phase change, and other industrial and commercial applications. The microcapsules of the invention display high strength and low leakage in environments such as in contact with solvent, detergents, shampoos, fabric softeners and surface cleaners. As a result, the microcapsules of the invention are suitable for use in such produces by being able to survive in such environments.

The microcapsule wall can serve the purpose of extending the shelf life, stabilize and protect the core material, mask strong flavors, or protect contents so that they are available to participate in reactions such as imaging of adhesive formation when the capsule wall is ruptured, sheared, fractured, broken or melted.

The core material is a benefit agent core material and can be a minor or major constituent of the material encapsulated by the microcapsules. If the core material can function as the oil or water solvent in the capsules, it is possible to make the core material the major or total material encapsulated. Usually, however, the core material is from 0.01 to 99 weight percent of the capsule internal contents, preferably 0.01 to about 64 by weight of the capsule internal contents, and more preferably from 0.1 to 45% by weight of the capsule internal contents. With certain especially potent materials or materials of high efficiency, the core can be at just trace quantities as compared to diluent or other materials in the core.

Useful benefit agent core materials include perfume raw materials, such as alcohols, ketones, aldehydes, esters, ethers, nitriles, alkenes, fragrances, fragrance solubilizers, essential oils, phase change materials, lubricants, colorants, cooling agents, preservatives, antimicrobial or antifungal actives, herbicides, antiviral actives, antiseptic actives, antioxidants, biological actives, deodorants, emollients, humectants, exfoliants, ultraviolet absorbing agents, self-healing compositions, corrosion inhibitors, sunscreens, silicone oils, waxes, hydrocarbons, higher fatty acids, essential oils, lipids, skin coolants, vitamins, sunscreens, antioxidants, glycerine, catalysts, bleach particles, silicon dioxide particles, malodor reducing agents, dyes, brighteners, antibacterial actives, antiperspirant actives, cationic polymers and mixtures thereof. Phase change materials useful as benefit agent core materials can include, by way of illustration and not limitation, paraffinic hydrocarbons having 13 to 28 carbon atoms, various hydrocarbons such n-octacosane, n-heptacosane, n-hexacosane, n-pentacosane, n-tetracosane, n-tricosane, n-docosane, n-heneicosane, n-eicosane, n-nonadecane, octadecane, n-heptadecane, n-hexadecane, n-pentadecane, n-tetradecane, n-tridecane. Phase materials can alternatively, optionally in addition include crystalline materials such as 2,2-dimethyl-1,3-propanediol, 2-hydroxymethyl-2-methyl-1,3-propanediol, acids of straight or branched chain hydrocarbons such as eicosanoic acid and esters such as methyl palm itate, fatty alcohols and mixtures thereof.

In the alternative embodiment, any of the heating steps in the microencapsulation process can be replaced with a UV or light induced or electron beam induced free radical generation step.

More particularly, in this alternative embodiment the invention is a process of obtaining microcapsules by dispersing an oil soluble polyfunctional (meth)acrylate monomer, an oil soluble bi- or polyfunctional vinyl monomer and chitosan with initiator in the water phase, along with a UV initiator in one or more of the oil and water phases. Optionally, a visible light induced free radical generator could also be used. This dispersion is subjected to UV light to form a prepolymer. To the internal phase oil, a water phase is added comprising a dispersion in water of an optimal anionic emulsifier. Optionally either a UV initiator or alternatively thermal initiator or alternatively no additional initiator is added to the water phase. The water phase is emulsified into the oil phase (W/O), or alternatively an excess of the water phase is used and the oil phase is emulsified into the water phase (O/W). Depending on the type of initiator or initiators, the dispersion is then subjected to UV light or heated (as appropriate to the initiator) to generate free radicals.

As polymerization progresses, microcapsule wall material forms at the interface of the water and oil phases. A third UV exposure or heating step is used to further polymerize or harden the formed wall material.

Similar substitution of UV initiator can be made in any of the microencapsulation processes described herein and by substitution of a respective UV exposure step for the respective thermal heating step. UV initiators include benzophenone; acetophenone; benzil; benzaldehyde; o-chlorobenzaldehyde; xanthone; thioxanthone; 9,10-anthraquinone; 1-hydroxycyclohexyl phenyl ketone; 2,2-diethoxyacetophenone; dimethoxyphenylacetophenone; methyl diethanolamine; dimethylam inobenzoate; 2-hydroxy-2-methyl-1-phenylpropane-1-one; 2,2-di-sec-butoxyacetophenone; 2,2-dimethoxy-1,2-diphenylethan-1-one; dimethoxyketal; and phenyl glyoxal.2,2'-diethoxyacetophenone, hydroxycyclohexyl phenyl ketone, alpha-hydroxyketones, alpha-aminoketones, alpha and beta naphthyl carbonyl compounds, benzoin ethers such as benzoin methyl ether, benzil, benzil ketals such as benzil dimethyl ketal, acetophenone, fluorenone, 2-hydroxy-2-methyl-1-phenylpropan-1-one. UV initiators of this kind are available commercially, e.g., IRGACURE 184™ or DEGACURE 1173™ from Ciba. Thermal initiators are available from DuPont. The fraction of the photoinitiator in any of the water or oil phase is approximately from about 0.1 to 10%, preferably 0.1 to about 6% by weight, more preferably 0.5 to 2.5 weight percent. Similar weight percent ranges can also be applied to the thermal initiators.

UV initiators can be included in substitution as an alternate initiator system (for any heating step or steps of the encapsulation process, or as an additional initiator system. This produces an initiator system for polymerization or oligomerization using a dual cure method or optional thermal or optional light or optional UV initiated method by appropriate selection of initiator and initiation method or methods. In an alternative embodiment of the invention, azo compounds that can be excited or split by UV light or high-energy radiation are used alone or in combination with thermal free radical initiators. In a yet alternative embodiment, the combination of thermal and UV initiators is formed only by azo compounds.

In a yet further embodiment, for specialized microencapsulation processes, the use of initiators, e.g., thioxanthones, phosphine oxides, metallocenes, tertiary aminobenzenes or tertiary aminobenzophenones, which break down into free radicals on exposure to visible light is effectively used. Such microencapsulation systems however typically require special handling of the system to prevent premature polymerization or oligomerization by appropriate control of lighting conditions.

For light activated microencapsulation, the use of UV initiators is preferred, or a combination of UV initiators and thermal free radical initiators. This combination can impart considerable versatility to the microencapsulation steps of the process where any step or steps of the microencapsulation process then can be initiated either by appropriate selection of an initiator decomposing at specific temperatures or decomposing under specific light conditions.

In a yet further embodiment, with appropriate selection of monomers and initiators, the respective monomers in the process can be polymerized or oligomerized using some suitable means such as heat (used with thermal initiators) or UV light (for use with UV initiators), or electron beam. When replacing the UV radiation with electron beam, the addition of additional initiators can be reduced. Options for individual heating steps of the encapsulation process include the freedom to use in substitution for any heating step, the use of visible light with suitable initiators, the use of UV light with suitable UV initiators, or ionizing radiation (e.g. electron beam or gamma ray) without added additional initiator or reduced amounts of initiator. All such means for purposes herein are intended by the terms "heating or exposing to actinin radiation."

UV initiators may be selected from those organic chemical compounds conventionally employed to promote UV-initiated formation of radicals. A preferred UV initiator is 1-hydroxycyclohexyl phenyl ketone because of the rapidity with which it generates free radicals when exposed to UV radiation. Mixtures of UV initiators or mixtures with thermal initiators may also be used. This is often desirable because it provides more efficient production of radicals in certain cases. In general, the UV initiator will be present in an amount of 0.1 to 10.0 weight percent in any of the water or oil phases, based on the total weight of all constituents. However, it is preferable to use between 0.5-2.5 weight percent UV initiator, most preferably 0.5-1.0 weight percent UV initiator, based on total weight.

The amount of each initiator, thermal, UV or light, that is employed can vary, and is dependent upon factors such as the monomer or oligomer material that is polymerized or further oligomerized. Typically, the amount of initiator ranges from about 0.1 to about 6 percent, and often about 1 to about 3 percent, based on the weight of all constituents.

In the following examples, the abbreviations correspond to the following materials:

TABLE 1

| | Company/City | |
|---|---|---|
| CD9055 | Sartomer, Exton, PA | acid acrylate adhesion promoter |
| CN975 | Sartomer, Exton, PA | hexafunctional urethane acrylate |
| Celvol 540 | Sekisui Specialty Chemicals, Secaucus, NJ | polyvinyl alcohol |

The examples herein are considered to illustrate the invention and should not be considered as limiting. In all the examples all percents, parts or proportions are by weight and all measurements are in the metric system unless otherwise indicated.

TABLE 2

| Example No. | Emulsifier Level (%) | Chitosan DDA (%) | Chitosan MW (kDa) | Slurry pH | Zeta Potential (mV) |
|---|---|---|---|---|---|
| 1 | 1.2 | N/A | N/A | 5.05 | −0.71 |
| 2 | 1.2 | 80-88 | 187 | 5.00 | 27.94 |
| 3 | 0 | 80-88 | 187 | 5.02 | 39.66 |
| 4 | 1.2 | 80-88 | 150 | 5.02 | 2.90 |
| 5 | 0 | 80-88 | 150 | 5.05 | 41.55 |
| 6 | 1.2 | >75 | 310->375 | 5.00 | 26.18 |
| 7 | 0 | >75 | 310->375 | 5.01 | 37.21 |
| 8 | 1.2 | 75-85 | 190-310 | 5.05 | 19.86 |
| 9 | 0 | 75-85 | 190-310 | 5.08 | 36.65 |
| 10 | 1.2 | 75-85 | 50-190 | 5.00 | 14.87 |
| 11 | 0 | 75-85 | 50-190 | 5.00 | 46.38 |
| 12 | 1.2 | 78.3 | 150 | 5.08 | 19.74 |
| 13 | 0 | 78.3 | 150 | 5.05 | 36.08 |

EXAMPLE 1

A first oil phase, consisting of 44.81 g perfume oil, 0.26 g tert-butylamino ethyl methacrylate, 0.26 g CD9055, and 21.51 g CN975 (Sartomer, Exton, PA) was prepared under mixing for 30 minutes at room temperature.

A second oil phase consisting of 78.51 g of the perfume oil, 100.89 g isopropyl myristate, 1.19 g 2,2'-azobis(2-methylbutyronitrile), and 0.96 g 4,4'-azobis[4-cyanovaleric acid] was added to a jacketed steel reactor. The reactor was held at 35° C. and the oil solution in mixed at 600 RPM's with a 2" flat mill blade while a nitrogen blanket is applied to the reactor at a rate of 0.1 SLPM. The solution was heated to 70° C. in 45 minutes and held at 70° C. for 45 minutes, before cooling to 50° C. in 75 minutes. At 50° C., the first oil phase was added to the reactor and the combined oils are mixed for 10 minutes at 50° C.

A water phase, containing 76.04 g Celvol 540 PVA (Sekisui Specialty Chemicals, Dallas, Tex.) at 5% solids, 240.72 g DI water, 1.43 g 4,4'-azobis[4-cyanovaleric acid], and 1.33 g NaOH at 21.5% was prepared and mixed until fully dissolved. After the oil phases pre-reacted together for 10 minutes at 50° C., mixing was ceased and the water phase mixture is added to the oil phases. High shear agitation was applied to produce an emulsion with the desired size characteristics. The temperature was increased to 75° C. in 30 minutes, held at 75° C. for 4 hours, increased to 95° C. in 30 minutes, and held at 95° C. for 6 hours. The batch was allowed to cool to room temperature. The microcapsules had a volume-weighted median size of 19.14 microns. The zeta potential at slurry pH ~5.00 was −0.71 mV.

EXAMPLE 2

Example 2 was prepared similarly to Example 1, except that chitosan replaced NaOH in the water phase. A water phase, containing 76.04 g Celvol 540 PVA (Sekisui Specialty Chemicals, Dallas, Tex.) at 5% solids, 240.72 g DI water, and 1.43 g 4,4'-azobis[4-cyanovaleric acid] was prepared and mixed over 45 minutes until the 4,4'-azobis[4-cyanovaleric acid] is dissolved into a cloudy solution. The pH of the water phase is 3.9, which allows an acidic environment for the subsequent addition of 2.4 g chitosan of molecular weight 187 kDa and 80-88% DDA. The water phase mixture with chitosan was then mixed for 2.5 hours followed by heating to 40° C. for 45 minutes, before proceeding as done in example 1. The volume-weighted median size was 13.51 microns, and zeta potential at slurry pH ~5.00 was 27.94 mV.

EXAMPLE 3

Example 3 was similarly prepared as Example 2, except the Celvol 540 PVA (Sekisui Specialty Chemicals, Dallas, Tex.) was removed from the formulation and the difference was replaced with DI water. The volume-weighted median size was 20.37 microns, and zeta potential at slurry pH ~5.00 was 39.66 mV.

EXAMPLE 4

Example 4 was made following the procedure of example 2 except that the chitosan was of molecular weight 150 kDa and 80-88% DDA. The volume-weighted median size was 16.90 microns, and zeta potential at slurry pH ~5.00 was 2.90 mV.

EXAMPLE 5

Example 5 was made following the procedure of example 3 except that the chitosan was of molecular weight 150 kDa and 80-88% DDA. The volume-weighted median size was 36.57 microns, and zeta potential at slurry pH ~5.00 was 41.55 mV.

EXAMPLE 6

Example 6 was made following the procedure of example 2 except that the chitosan was of molecular weight 310->375 kDa and >75% DDA. The volume-weighted median size was 23.36 microns, and zeta potential at slurry pH ~5.00 was 26.18 mV.

EXAMPLE 7

Example 7 was made following the procedure of example 3 except that the chitosan was of molecular weight 310->375 kDa and >75% DDA. The volume-weighted median size was 13.51 microns, and zeta potential at slurry pH ~5.00 was 37.21 mV.

EXAMPLE 8

Example 8 was made following the procedure of example 2 except that the chitosan was of molecular weight 190-310 kDa and 75-85% DDA. The volume-weighted median size was 11.93 microns, and zeta potential at slurry pH ~5.00 was 19.86 mV.

EXAMPLE 9

Example 9 was made following the procedure of example 3 except that the chitosan was of molecular weight 190-310 kDa and 75-85% DDA. The volume-weighted median size was 17.76 microns, and zeta potential at slurry pH ~5.00 was 36.65 mV.

EXAMPLE 10

Example 10 was made following the procedure of example 2 except that the chitosan was of molecular weight 50-190 kDa and 75-85% DDA. The volume-weighted median size was 14.92 microns, and zeta potential at slurry pH ~5.00 was 14.87 mV.

EXAMPLE 11

Example 11 was made following the procedure of example 3 except that the chitosan was of molecular weight 50-190 kDa and 75-85% DDA. The volume-weighted median size was 30.72 microns, and zeta potential at slurry pH ~5.00 was 46.38 mV.

EXAMPLE 12

Example 12 was made following the procedure of example 2 except that the chitosan was of molecular weight 150 kDa and 78.3% DDA. The volume-weighted median size was 10.41 microns, and zeta potential at slurry pH ~5.00 was 19.74 mV.

EXAMPLE 13

Example 13 was made following the procedure of example 3 except that the chitosan was of molecular weight 150 kDa and 78.3% DDA. The volume-weighted median size was 14.56 microns, and zeta potential at slurry pH ~5.00 was 36.08 mV.

All documents cited in the specification herein are, in relevant part, incorporated herein by reference for all jurisdictions in which such incorporation is permitted. The citation of any publication is for its disclosure prior to the filing date and should not be construed as an admission that such publication is prior art or that the present invention is not entitled to antedate such publication by virtue of prior invention. To the extent that any meaning or definition of a term in this document conflicts with any meaning or definition of the same term in a document incorporated by reference, the meaning or definition assigned to that term in this document shall govern.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 microns" is intended to mean "about 40 microns".

Uses of singular terms such as "a," "an," are intended to cover both the singular and the plural, unless otherwise indicated herein or clearly contradicted by context. The terms "comprising," "having," "including," and "containing" are to be construed as open-ended terms. Any description of certain embodiments as "preferred" embodiments, and other recitation of embodiments, features, or ranges as being preferred, or suggestion that such are preferred, is not deemed to be limiting. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention. No unclaimed language should be deemed to limit the invention in scope. Any statements or suggestions herein that certain features constitute a component of the claimed invention are not intended to be limiting unless reflected in the appended claims.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive variations and charges can be made by those skilled in the art without departing from the spirit and scope of the invention.

What is claimed is:

1. A population of microcapsules comprising a core material surrounded by a wall material comprising the reaction product of firstly a polysaccharide having pendant amine groups reactive with an initiator of formula 1, and secondly at least one multifunctional (meth)acrylate monomer free radically polymerized with the same initiator of formula 1

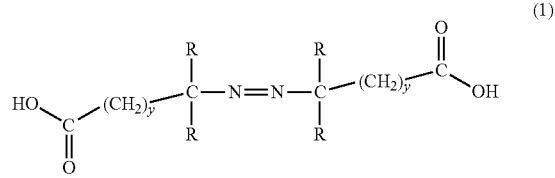

wherein each R is independently selected from hydrogen, $C_1$ to $C_8$ alkyl, or a cyano group; wherein each y is independently an integer from 1 to 8.

2. The population of microcapsules according to claim 1 wherein the polysaccharide is chitosan.

3. The population of microcapsules according to claim 2 wherein the chitosan has a degree of deacetylation of at least 50%.

4. The population of microcapsules according to claim 1 wherein the wall material comprises greater than 50 wt % of multifunctional (meth)acrylate.

5. The population of microcapsules according to claim 1 wherein the multifunctional (meth)acrylate is selected from the group consisting of di-, tri-, tetra-, penta-, hexa-, hepta-, or octa-functional acrylate or methacrylate esters, multifunctional urethane acrylate or methacrylate esters, and epoxy acrylates or methacrylates.

6. The population of microcapsules according to claim 1 wherein the wall material comprises 0.1 to 20% by weight polysaccharide.

7. The population of microcapsules according to claim 1 wherein the wall material comprises a polymer obtained by polymerization of:
   0.1 to 80% by weight of multifunctional (meth)acrylate monomer;
   0.1 to 60% by weight of the polysaccharide; and
   0.1 to 30% by weight of the initiator of formula 1.

8. The population of microcapsules according to claim 1 comprising in addition an aqueous medium into which the microcapsules are dispersed forming a slurry, said slurry having a zeta potential greater than 0 millivolts when measured at a pH of 5.

9. A process of forming a population of microcapsules comprising a core material, and a wall material surrounding the core material, the wall material comprising the reaction product of a polysaccharide having one or more amine groups, and a multifunctional (meth)acrylate monomer, the microcapsule population formed by:
   providing a water phase comprising a polysaccharide having a pendant amine group and a first initiator of formula 1,

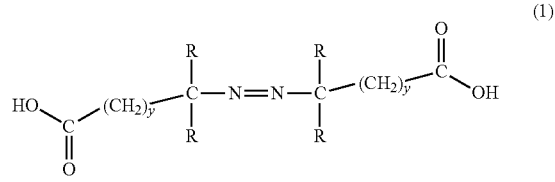

wherein each R is independently selected from hydrogen, $C_1$ to $C_8$ alkyl, or a cyano group; wherein each y is independently an integer from 1 to 8,
the first initiator having a carboxyl functional group and a free radical azonitrile moiety;
providing an oil phase and dispersing or dissolving a core material into the oil phase;
dispersing a multifunctional (meth)acrylate monomer, and optionally a second initiator, into the oil phase;
combining the oil phase with the water phase; and
heating or exposing to actinic radiation the combined oil phase and water phase, to activate the initiator of the water phase to generate free radicals and to polymerize the multifunctional methacrylate monomer, and adjusting the pH such that the carboxyl functional group of the first initiator reacts with the amine groups of the polysaccharide.

10. A process for forming a population of microcapsules comprising a core material, chitosan and a (meth)acrylate wall material surrounding the core material, the microcapsule population being formed by:
providing a benefit agent core material comprising an oil soluble fluid material or oil-dispersible solid particle dispersed in an oil soluble fluid material;
providing an oil internal phase comprising a diluent;
dividing the oil internal phase into oil 1 and oil 2;
dispersing into an oil 1 an initiator;
dispersing into an oil 2 a multifunctional (meth)acrylate monomer or oligomer, and optimally one or more acrylates selected from the group consisting of monofunctional acrylates, difunctional (meth)acrylate esters and polyfunctional (meth)acrylate esters, and dispersing into oil 2 an oil soluble fluid core material or oil-dispersible solid particle core material dispersed in a fluid core material;
heating or exposing to actinic radiation sufficiently to activate the initiator of oil 1;
combining oil 1 and oil 2 forming a combined oil continuous internal phase and allowing reaction to proceed for a time sufficient to pre-polymerize the multifunctional monomers or oligomers from oil 2;
providing a water phase comprising chitosan and a water soluble or dispersible initiator of formula 1

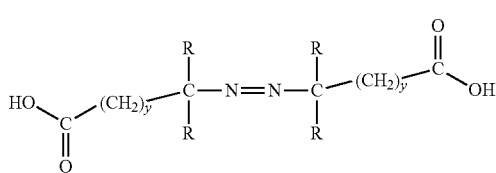

(1)

wherein each R is independently selected from hydrogen, $C_1$ to $C_8$ alkyl, or a cyano group; wherein each y is independently an integer from 1 to 8;
heating or exposing to actinic radiation sufficiently to activate the initiator of the water phase;
forming a chitosan and (meth)acrylate mixture by dispersing the combined oil internal phase into the water phase;
emulsifying the chitosan and (meth)acrylate mixture by subjecting the mixture to high shear agitation;
heating or exposing to actinic radiation the chitosan and (meth)acrylate mixture for a time and temperature sufficient whereby the multifunctional (meth)acrylate and chitosan bond and migrate to the interface of the oil and water phases thereby surrounding the core material in the oil phase and forming wall material.

11. The process according to claim 10 wherein the initiator according to formula 1 is 4,4'-azobis (4-cyanopentanoic acid).

12. The process according to claim 10 wherein the chitosan has a degree of deacetylation of at least 75%.

13. The process according to claim 10 wherein the microcapsule wall contains 0.01 to 14% by weight of chitosan.

14. The process according to claim 10 wherein the chitosan is partially deacetylated.

15. The process according to claim 10 wherein the chitosan is a D, L lactic acid chitosan.

16. The process according to claim 10 wherein the chitosan is a glycolic acid chitosan.

17. The process according to claim 10 wherein the chitosan is selected from the group of water soluble chitosans selected from glycerol chitosan, hydrolyzed chitosan, n-hydroxypropyl chitosan, polyoxyalkylene chitosan, and chitosan oligosaccharide.

18. The process according to claim 10 wherein the chitosan is comprised of D-glucosamine and N-acetyl glucosamine moieties, and the ratio of D-glucosamine to N-acetyl glucosamine is 3:1 or greater.

19. The process according to claim 10 wherein the oil internal phase is isopropyl myristate.

20. The process according to claim 10 wherein the core material is selected from a biological active, a dye, a perfume, a fragrance, a phase change material, a lubricant, or a chromogen.

21. The process according to claim 10 wherein the multifunctional (meth)acrylate is selected from the group consisting of mono-, di-, tri-, tetra-, penta-, hexa-, hepta-, or octa-functional acrylate or methacrylate esters, multi-functional urethane acrylate or methacrylate esters, and epoxy acrylates or methacrylates.

* * * * *